(12) United States Patent
Guo et al.

(10) Patent No.: US 11,744,468 B2
(45) Date of Patent: Sep. 5, 2023

(54) GENERAL B-MODE SURFACE IMAGING

(71) Applicant: The Johns Hopkins University, Baltimore, MD (US)

(72) Inventors: Xiaoyu Guo, Baltimore, MD (US); Emad M. Boctor, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 708 days.

(21) Appl. No.: 15/499,105

(22) Filed: Apr. 27, 2017

(65) Prior Publication Data

US 2017/0311809 A1 Nov. 2, 2017

Related U.S. Application Data

(60) Provisional application No. 62/328,532, filed on Apr. 27, 2016.

(51) Int. Cl.
| | |
|---|---|
| *A61B 5/00* | (2006.01) |
| *A61B 8/00* | (2006.01) |
| *A61B 5/08* | (2006.01) |
| *A61B 8/08* | (2006.01) |

(52) U.S. Cl.
CPC .......... *A61B 5/0095* (2013.01); *A61B 8/4494* (2013.01); *A61B 8/5207* (2013.01); *A61B 8/54* (2013.01)

(58) Field of Classification Search
CPC ....... A61B 5/0095; A61B 8/54; A61B 8/5207; A61B 8/4494; A61B 5/0059; A61B 5/0082; A61B 8/52; A61B 2090/378; A61B 2034/206; A61N 2007/0086; A61N 7/0022; G01N 29/2418; G01N 29/0681; G01N 21/1702; G06T 11/203; G06T 11/20; G06T 11/00; G06T 17/10; G06T 5/006; G06T 5/00; G06T 7/557; G02B 21/244; G02B 27/0025; B06B 1/06; B06B 1/0622; B06B 1/0629; G01S 7/52017–5209

See application file for complete search history.

(56) References Cited

U.S. PATENT DOCUMENTS

| | | | | |
|---|---|---|---|---|
| 6,014,473 A | * | 1/2000 | Hossack | A61B 8/145 348/169 |
| 6,135,956 A | * | 10/2000 | Schmiesing | G01S 7/52025 600/437 |
| 6,503,199 B1 | * | 1/2003 | Lennon | G01S 7/52085 128/916 |
| 9,730,676 B2 | * | 8/2017 | Brown | A61B 8/5207 |
| 10,321,889 B2 | * | 6/2019 | Wegner | G09B 23/28 |

(Continued)

*Primary Examiner* — Joel Lamprecht
*Assistant Examiner* — Amy Shafqat
(74) *Attorney, Agent, or Firm* — Harrity & Harrity, LLP

(57) ABSTRACT

An ultrasound system includes an ultrasound transducer, an ultrasound controller structured to communicate with the ultrasound transducer, and a signal processing system structured to communicate with the ultrasound transducer. The ultrasound controller is structured to provide control signals to the ultrasound transducer to transmit a plurality of at least three non-coplanar A-line signals and to receive corresponding at least three non-coplanar A-line signals, and the signal processing system is structured to receive the at least three non-coplanar A-line signals from the ultrasound transducer and to form a generalized B-mode image based on the at least three non-coplanar A-line signals.

35 Claims, 7 Drawing Sheets

(56) References Cited

U.S. PATENT DOCUMENTS

| | | | |
|---|---|---|---|
| 2011/0275890 A1* | 11/2011 | Wang | A61B 5/0062 |
| | | | 600/104 |
| 2012/0076681 A1 | 3/2012 | Stoianovici et al. | |
| 2012/0229682 A1* | 9/2012 | Ng | H04N 9/646 |
| | | | 348/241 |
| 2013/0197824 A1* | 8/2013 | Baba | G01S 15/8927 |
| | | | 702/39 |
| 2014/0024928 A1 | 1/2014 | Boctor et al. | |
| 2015/0173713 A1* | 6/2015 | Oikawa | A61B 8/54 |
| | | | 600/447 |
| 2016/0374562 A1* | 12/2016 | Vertikov | A61B 1/0005 |
| | | | 600/424 |
| 2018/0133756 A1* | 5/2018 | Rothberg | G10K 11/18 |
| 2019/0357877 A1* | 11/2019 | Courtney | G10K 11/352 |

\* cited by examiner

GENERAL B-MODE SURFACE IMAGING

CROSS-REFERENCE TO RELATED APPLICATIONS

This application claims priority benefit from U.S. provisional patent application No. 62/328,532, filed on Apr. 27, 2016, the entire content of which is incorporated herein by reference. All references cited anywhere in this specification, including the Background and Detailed Description sections, are incorporated by reference as if each had been individually incorporated.

BACKGROUND

1. Field

The field of some embodiments of this disclosure relates to ultrasound imaging systems and methods, and more particularly to ultrasound imaging systems and methods that provide generalized B-mode imaging. The field of further embodiments of this disclosure relates to ultrasound imaging systems and ultrasound probes, and more particularly to ultrasound imaging systems that have magnetic-resonance-imaging-compatible (MRI-compatible) ultrasound probes and to MRI-compatible ultrasound probes.

2. Background

In ultrasound imaging, various imaging techniques are used including A-mode and B-mode imaging. The A-mode, also referred to as 1D-mode or Amplitude Modulation, is a one-dimensional presentation of a reflected sound wave in which echo amplitude is displayed in the vertical axis (y-axis) and the echo-delay representative of depth is displayed on the horizontal axis (x-axis). In A-mode, a single transducer transmits along a line through the body with the received echoes plotted on a screen as a function of depth. The B-mode, also referred to as 2D-mode or Brightness Modulation, is a two-dimensional representation of ultrasound data in which the intensity of the echo sound wave is represented by the modulation of brightness. Thus, the brightness depends on the amplitude or intensity of the echo. In B-mode, a linear array of transducers simultaneously transmits and receives along a plane through the body that can be viewed as a two-dimensional image on a screen. In B-mode, data is not represented on the y-axis, instead the data is represented on the z-axis which represents the intensity or amplitude of the echo and the x-axis represents depth. B-mode displays an image of larger and smaller dots which represent stronger and weaker echoes, respectively.

Three-dimensional (3D) ultrasound imaging, also referred to as C-mode, is also widely used in the medical diagnostic area. Currently, the dominant method for 3D ultrasound image acquisition is using a wobbler scanning probe. In these probes, a one-dimensional (1D) array is used to generate two-dimensional (2D) B-mode images. The array is driven by a motor, mechanically scanning along the lateral direction. As a result, a series of B-mode slices can be acquired to form the 3D image. As a replacement of the wobbler probe, a 2D array, also called a matrix array, has recently become commercially available. It is composed of a much larger number of transducer elements which is permutated as a 2D array. The mechanical scanning is replaced by electronic steering or scanning, for example by using phased array techniques. The purpose of performing volume imaging is to acquire the spatial information of the target. There are several problems with 3D ultrasound imaging, as follows:

1. Rendering and displaying a 3D ultrasound image is usually difficult. The most-often used methods include: a) x-y, y-z, z-x plane slice display. b) Threshold display. c) Semi-transparent 3D display. d) Elasticity based volume rendering.
2. The scanning speed or volume rate is low. Since the probe needs to acquire multiple A-mode lines for each image slice (128 or more in many cases), a volume image contains a large number of A-lines and takes a long time to acquire.
3. The data size is big. A 3D ultrasound image contains much more data than the 2D B-mode image.

Therefore, there remains a need for improved ultrasound imaging systems and methods.

SUMMARY OF THE DISCLOSURE

An ultrasound system according to some embodiments of the current disclosure includes an ultrasound transducer, an ultrasound controller structured to communicate with the ultrasound transducer, and a signal processing system structured to communicate with the ultrasound transducer. The ultrasound controller is structured to provide control signals to the ultrasound transducer to transmit a plurality of at least three non-coplanar A-line signals and to receive corresponding at least three non-coplanar A-line signals, and the signal processing system is structured to receive the at least three non-coplanar A-line signals from the ultrasound transducer and to form a generalized B-mode image based on the at least three non-coplanar A-line signals.

A method of obtaining an ultrasound image of a region of interest of a body under observation according to some embodiments of the current disclosure includes obtaining a plurality of at least three non-coplanar A-line images of the region of interest, and forming a generalized B-mode image using the plurality of at least three non-coplanar A-line images of the region of interest. The plurality of at least three non-coplanar A-line images are selected to at least substantially coincide with at least a portion of a surface of the region of interest.

An ultrasound probe according to some embodiments of the current disclosure includes an optical fiber that carries optical pulses to generate photoacoustic signals in a medium of interest, a mechanical scanning assembly coupled to the optical fiber to move a transmitting end of the optical fiber with at least one degree of motion, and an ultrasound receiver configured to receive reflected, backscattered or transmitted ultrasound waves An ultrasound system according to some embodiments of the current disclosure includes an MRI-compatible ultrasound probe, an ultrasound controller configured to communicate with the MRI-compatible ultrasound probe, and a signal processing system configured to communicate with the MRI-compatible ultrasound probe. The MRI-compatible ultrasound probe includes an all-optical ultrasound transducer that is scan-able in at least one degree of freedom.

A magnetic resonance imaging system (MRI) compatible ultrasound probe according to some embodiments of the current disclosure includes an all-optical ultrasound transducer, and an MRI compatible mechanical scanning assembly coupled to at least a component of the optical ultrasound transducer. The all-optical ultrasound transducer includes an optical fiber that carries optical pulses to generate photoacoustic signals in a medium of interest, and a Fabry-Perot interferometer at a transmission-reception end of the all-optical ultrasound transducer. The MRI compatible mechanical scanning assembly includes at least one MRI-compatible pneumatic stepper motor operatively connected to the optical fiber to move the transmission-reception end of the all-optical ultrasound transducer with at least one degree of motion provided by the at least one MRI-compatible pneumatic stepper motor.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

Some embodiments of the current disclosure are discussed in detail below. In describing embodiments, specific terminology is employed for the sake of clarity. However, the disclosure is not intended to be limited to the specific terminology so selected. A person skilled in the relevant art will recognize that other equivalent components can be employed and other methods developed without departing from the broad concepts of the current disclosure. All references cited anywhere in this specification, including the Background and Detailed Description sections, are incorporated by reference as if each had been individually incorporated.

The terms "light" and "optical" are intended to have a broad meaning. They can include, but are not limited to, the visible regions of the electromagnetic spectrum. They can also include nonvisible regions of the electromagnetic spectrum such as infrared and ultraviolet light, as well as visible regions.

The term "photoacoustic" is intended to have a broad definition which can be photons at any energy suitable for the particular application that deposit energy that generates an acoustic signal in a body of interest.

The term "body" refers generally to a mass, and not specifically to a human or animal body. In some applications, the body of interest can be a human or animal organ, or a portion thereof.

The term A-line in reference to ultrasound imaging refers to processing ultrasound data from a single transmitter-receiver pair along a linear path through the body of interest. The transmitter-receiver pair could be at the same, or close to the same location. They could be separate components or a transceiver that can operate alternately in transmit and receive modes. In some embodiments, the transmitter and receiver can be separate components in different locations, for example such that the receiver receives transmitted ultrasound energy rather than reflected ultrasound energy.

Conventional B-mode images are usually constructed from a plurality of A-lines all substantially within a plane. Three-dimensional images, also referred to as C-mode images, are usually constructed from a plurality of conventional B-mode slices.

In many ultrasound applications, only one segment slice in the 3D ultrasound image is needed. However, in many cases, the segment is not on a flat plane. Under conventional approaches, the entire volume data has to be acquired to extract the desired image slice. However, such an approach leads to inefficient data acquisition and processing when only a non-planar 2D ultrasound image is desired. Therefore, some embodiments of the current disclosure provide a General B-mode Surface (GB surface) imaging approach, by which the spatial information of interest of the target can be acquired without imaging the entire volume.

Figure 1:
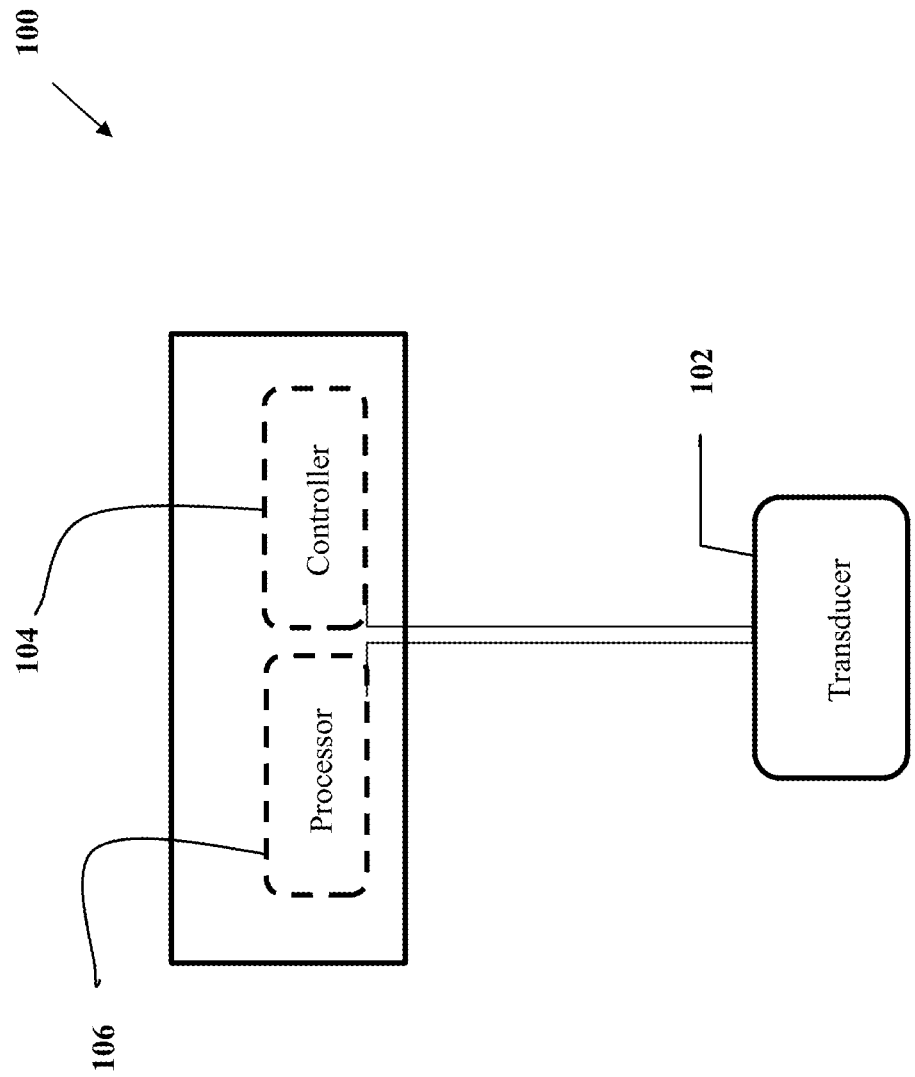
FIG. 1 is a schematic illustration of an ultrasound system, according to an embodiment of the current disclosure.

FIG. 1 is a schematic illustration of an ultrasound system 100 according to an embodiment of the current disclosure. The ultrasound system 100 includes an ultrasound transducer 102, an ultrasound controller 104 configured to communicate with the ultrasound transducer 102, and a signal processing system 106 also configured to communicate with the ultrasound transducer 102. In some embodiments, the signal processing system 106 can also communicate with the ultrasound controller 104.

The ultrasound controller 104 is structured to provide control signals to the ultrasound transducer 102 to transmit a plurality of at least three non-coplanar A-line signals and to receive corresponding at least three non-coplanar A-line signals. The signal processing system 106 is structured to receive the at least three non-coplanar A-line signals from the ultrasound transducer 102 and to form a generalized B-mode image based on the at least three non-coplanar A-line signals.

The signal processing system 106 can be or include a signal processor, for example. In some embodiments, it can include a plurality of signal processors either packaged together as a single device and/or distributed over a network, for example. The signal processor can be programmable, for example with loaded software, and/or hard wired to perform the signal processing functions. Some examples of hard-wired signal processors can be, but are not limited to, ASICs, FPGAs, and the like. Although not shown in FIG. 1, the ultrasound system 100 can also include memory, data storage and/or display devices which can be selected from currently available and/or future developed devices without limitation to the general concepts of the current disclosure.

The GB surface, according to some embodiments of the current disclosure, is approximated by the at least three non-coplanar A-lines. The A-lines can be, but are not required to be parallel to each other. Furthermore, there can be a relatively large number of A-lines in a GB surface so as to provide a high resolution ultrasound image of a surface that could have a complex contour. In some applications, a GB surface could be selected such that it coincides with a structure of interest such as, but not limited to, a portion of bone, a portion of an internal organ, or a tissue surface, for example.

Figure 3:
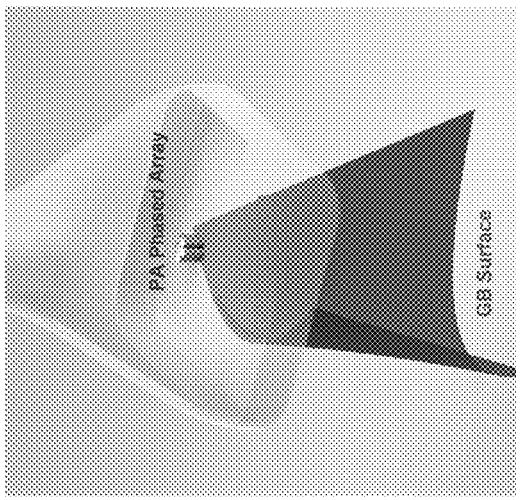
FIG. 3 is a schematic illustration of an ultrasound probe, according to another embodiment of the current disclosure.
Figure 2:
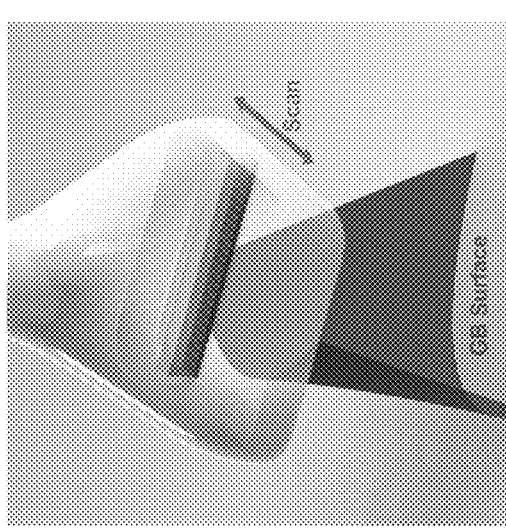
FIG. 2 is a schematic illustration of an ultrasound probe, according to an embodiment of the current disclosure.
Figure 5:
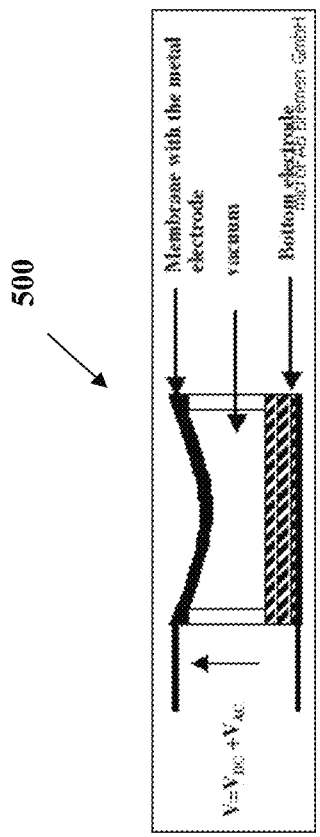
FIG. 5 is a schematic illustration of a capacitive micromachined ultrasonic transducer (CMUT) that can be used in ultrasound probes, according to some embodiments of the current disclosure.
Figure 4:
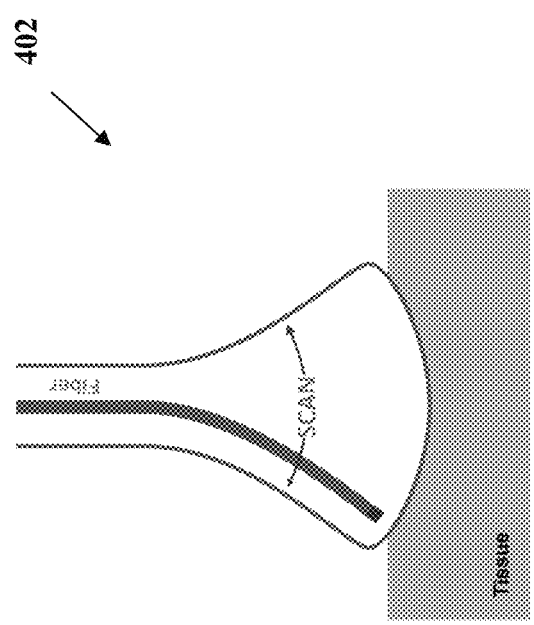
FIG. 4 is a schematic illustration of an ultrasound probe, according to another embodiment of the current disclosure.

FIGS. 2, 3 and 4 provide schematic illustrations of some embodiments 202, 302, 402 of the ultrasound transducer 102. However, the general concepts of the current disclosure are not limited to only these particular embodiments. In particular, FIG. 2 illustrates an embodiments 202 of ultrasound transducer 102 in which it has a linear array which can be scanned back and forth as is represented schematically in the figure. Elements within the linear array can be actuated in sequence by ultrasound controller 104 to form a selected GB surface, for example. In other embodiments, the elements within the linear array can be actuated with specific phase relationships by ultrasound controller 104 so as to provide electronic steering to provide further control of directing A-lines to form the GB surface. This embodiment thus includes both mechanical control as well as electronic control to select timing, position and angles of the A-lines to form the GB surfaces. Another embodiment could include a two-dimensional array of transducer elements either with or without mechanical structures to move the array. The transducers can be electrically actuated transducers, such as, but not limited to, piezoelectric elements, for example. In other embodiments, the ultrasound transducer 102 can include photo acoustic and/or thermo acoustic transducer elements. In other embodiments, one or more capacitive micro-machined ultrasonic transducers (CMUTs) can be used. FIG. 5 is a schematic illustration of a CMUT 500. In some embodiments, the ultrasound transmitters and receivers described in U.S. patent application Ser. No. 13/943,649 (assigned to the same assignee as the current application) can be used. The entire content of U.S. patent application Ser. No. 13/943,649, published as US2014/0024928, is incorporated herein by reference.

A capacitive micro-machined ultrasonic transducer (CMUT) is a MEMS (micro electro-mechanical systems) type of ultrasound transducer that is fabricated on semiconductor chips. The basic concept is to create micro capacitors with one side of the electrode plates working as a vibration membrane. Acoustic waves drive the membrane electrode plate and the vibration is converted to an electrical signal that can be picked up. Alternatively, by applying an electrical signal to the CMUT cell, it also works as a transmitter to emit ultrasound waves. An embodiment of an optical imaging probe combines a photoacoustic ultrasound source with a CMUT as a receiver. Silicon is transparent to infrared light with wavelength longer than about 1 µm. In photoacoustic systems, 1.064 µm is a common wavelength for the light sources. The CMUTs device can thus be transparent to the photoacoustic light. In such an imaging probe, the photoacoustic light is delivered through the plate of the CMUT. It then generates ultrasound pulses on either the body of interest or a photoacoustic sensitive material layer. The ultrasound pulses propagate inside the body of interest, and the reflected signal is detected by the CMUT. In some applications, the photoacoustic sensitive material layer is not necessary. In that case, the light is directly absorbed by the body of interest to generate the photoacoustic signal. In both of these two configurations, the CMUT functions as a receiver only. However, the membrane electrode can also be made of or coated with light absorptive material. In this case the photoacoustic light penetrates the substrate of the CMUT, but is absorbed by the CMUT cell membrane to generate an acoustic signal. In this configuration the CMUT device works as both the transmitter and receiver.

In some embodiments, the GB surface can be selected by first producing a 3D ultrasound image and using it to identify the surface of interest. In other embodiments, previously acquired data, such as, but not limited to, preoperative data, could be used to select a GB surface to be imaged by ultrasound. In some embodiments, data from imaging modalities other than, or in addition to, ultrasound data can be used for selecting a GB surface.

In FIGS. 2 and 3, the dark shaded regions represent the GB-surfaces under General B-mode imaging. Each GB surface has a series of A-mode lines that are oriented in different directions and that start from different positions. FIG. 2 has a linear wobbler probe running on the GB-mode. The A-line start position varies by shifting the transmitter (Tx) aperture. FIG. 3 is an example of an all-optical imaging probe running on the GB-mode. The phased array moves on the bottom surface of the probe with two degrees of freedom (2-DOF).

As noted above, FIG. 2 illustrates an embodiment of the GB-mode with a mechanical wobbler probe. During the scanning, instead of acquiring a complete B-mode image, the array only images one A-mode line at each position. These A-mode lines are not necessarily perpendicular to the array. They can be electronically steered within each array plane. The angle and position of these A-lines vary gradually during the scanning. As a result, a GB-mode image within the curved surface shown in the figure is acquired. Because we are only imaging one line at each position, the scanning speed can be much faster than the conventional volume imaging, and the data size is also reduced. The acquired data can be used to form a GB-mode image within the curved surface. Since the image is a two-dimensional image, i.e., a curved two-dimensional surface, it is easy to display or print out. In many conventional 3D ultrasound imaging applications, the volume data is acquired just for extracting a curvy structure, like an organ surface or a vessel. In these cases, the GB surface scan method can be a more efficient alternative.

If the imaging probe has a 2D or 1.5D matrix array, the beam steering is not limited to one plane. In this case, the GB surface can be formed with scan lines along any direction. Theoretically, the GB surface can be any ruled surface, which is mathematically defined as a surface on which every point has a straight line that lies on this surface. In reality, due to the limited array aperture and steering capability, not all ruled surfaces can be achieved by the GB scan.

FIG. 4 is a schematic illustration of an all-optical fiber scanning imaging probe 402 which can be used for ultrasound transducer 102 according to an embodiment of the current disclosure. This is an embodiment of an ultrasound GB surface scan probe based on a photoacoustic transmitter and a fiber-optical ultrasound receiver. The optical ultrasound transmission and receiving methods have been described previously in U.S. patent application Ser. No. 13/943,649 incorporated by reference herein. As shown in FIG. 4, a single element optical ultrasound element is in the 2D probe enclosure. The element is mechanically driven by motors with two degree of freedom, moving on the inner side of the probe coupling surface. The routine along which the ultrasound element scans can be pre-programmed based on the target structure. Furthermore, the ultrasound probe 402 can be completely MRI compatible if MRI compatible motors are used. For example, the pneumatic stepper motor described in U.S. Pub. No. 2012/0076681 (U.S. application Ser. No. 13/270,692) to the same assignee as the assignee of the current application, the entire content of which is incorporated herein by reference, can be used for the above-noted mechanically driven motors to provide a fully MRI compatible ultrasound probe.

In some embodiments, the single optical ultrasound element can be replaced with a multiple element array. By controlling the transmitter and receiver time delay of each element, it works as a ultrasound phased array. Depending on the number of elements and the geometric configuration, it could be a 1D or 2D array. The phased array enables one or two degree of beam steering freedom. Theoretically, one can acquire a B-mode image within any GB surface.

MRI-Compatible Ultrasound Probes

Figure 6:
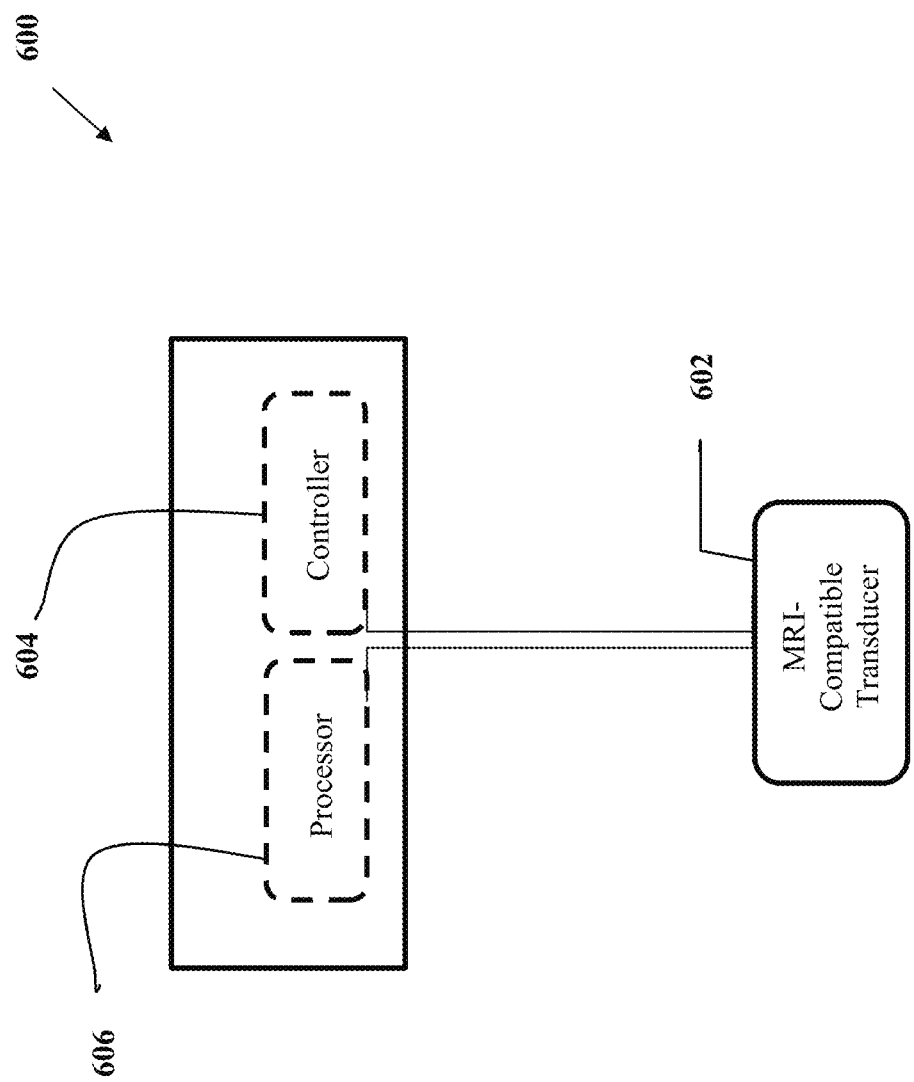
FIG. 6 is a schematic illustration of an ultrasound system, according to an embodiment of the current disclosure.

FIG. 6 is a schematic illustration of an ultrasound system 600 according to another embodiment of the current disclosure. The ultrasound system 600 includes an MRI-compatible ultrasound probe 602, an ultrasound controller 604 configured to communicate with the MRI-compatible ultrasound probe 602, and a signal processing system 606 also configured to communicate with the MRI-compatible ultrasound probe 602. In some embodiments, the signal processing system 606 can also communicate with the ultrasound controller 604. The MRI-compatible ultrasound probe 602 has at least one all-optical ultrasound transducer that can be scanned in at least one degree of freedom.

The ultrasound system 600 can be configured to provide conventional A-mode, B-mode and/or three-dimensional ultrasound images. In some embodiments, the ultrasound controller 604 can also be structured to provide control signals to the MRI-compatible ultrasound probe 602 to transmit a plurality of at least three non-coplanar A-line signals and to receive corresponding at least three non-coplanar A-line signals. In some embodiments, the signal processing system 606 can be structured to receive the at least three non-coplanar A-line signals from the MRI-compatible ultrasound probe 602 and to form a generalized B-mode image based on the at least three non-coplanar A-line signals. Although the ultrasound system 600 can be configured to provide General B-Mode imaging, the general concepts of the current disclosure are not limited to only General B-Mode imaging.

In many ultrasound applications, only one segment slice in the 3D ultrasound image is needed. However, in many cases, the segment is not on a flat plane. Under conventional approaches, the entire volume data has to be acquired to extract the desired image slice. However, such an approach leads to inefficient data acquisition and processing when only a non-planar 2D ultrasound image is desired. Therefore, some embodiments of the current disclosure provide a General B-mode Surface (GB surface) imaging approach, by which the spatial information of interest of the target can be acquired without imaging the entire volume.

The GB surface, according to some embodiments of the current disclosure, is approximated by the at least three non-coplanar A-lines. The A-lines can be, but are not required to be parallel to each other. Furthermore, there can be a relatively large number of A-lines in a GB surface so as to provide a high resolution ultrasound image of a surface that could have a complex contour. In some applications, a GB surface could be selected such that it coincides with a structure of interest such as, but not limited to, a portion of bone, a portion of an internal organ, or a tissue surface, for example.

The signal processing system 606 can be, or can include, a signal processor, for example. In some embodiments, it can include a plurality of signal processors either packaged together as a single device and/or distributed over a network, for example. The signal processor can be programmable, for example with loaded software, and/or hard wired to perform the signal processing functions. Some examples of hard-wired signal processors can be, but are not limited to, ASICs, FPGAs, and the like. Although not shown in FIG. 6, the ultrasound system 600 can also include memory, data storage and/or display devices which can be selected from currently available and/or future developed devices without limitation to the general concepts of the current disclosure.

Figure 8:
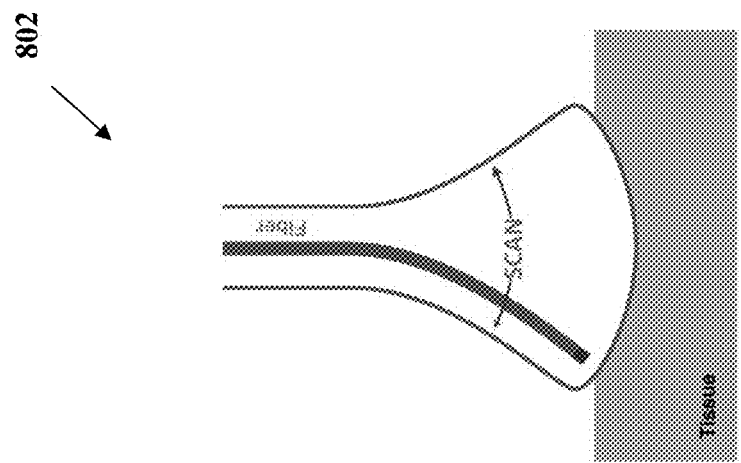
FIG. 8 is a schematic illustration of an ultrasound probe, according to another embodiment of the current disclosure.
Figure 7:
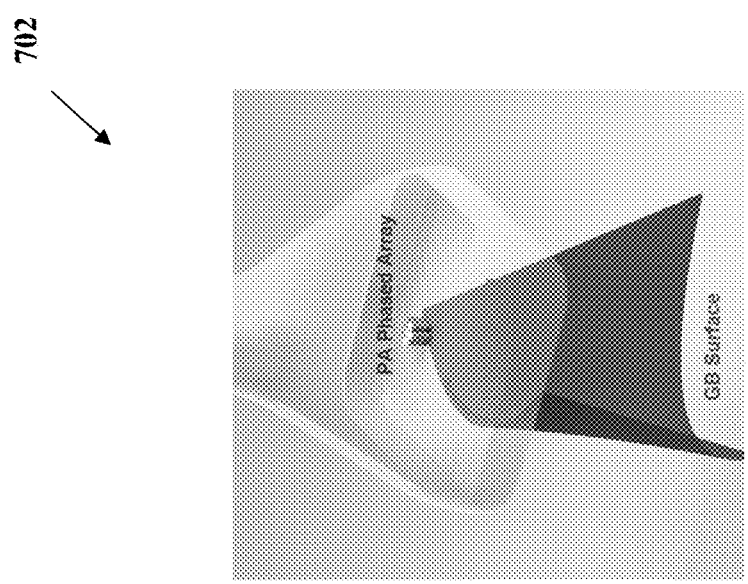
FIG. 7 is a schematic illustration of an ultrasound probe, according to an embodiment of the current disclosure.

FIGS. 7 and 8 provide schematic illustrations of embodiments 702 and 802 of the MRI-compatible ultrasound probe 602. However, the general concepts of the current disclosure are not limited to only these particular embodiments. In particular, FIG. 7 illustrates an embodiment 702 of MRI-compatible ultrasound probe 602 in which it has a photoacoustic phased array. Elements within the linear array can be actuated in sequence by ultrasound controller 604. The embodiments of FIGS. 7 and 8 include both mechanical control as well as at least one all-optical ultrasound transducer. Another embodiment could include a two-dimensional array of all-optical transducer elements without mechanical structures to move the array. In some embodiments, the ultrasound transmitters and receivers described in U.S. patent application Ser. No. 13/943,649 (assigned to the same assignee as the current application) can be used. The entire content of U.S. patent application Ser. No. 13/943,649, published as US2014/0024928, is incorporated herein by reference.

If the imaging probe has a 2D or 1.5D matrix array, the beam steering is not limited to one plane. In this case, a GB surface could be formed with scan lines along any direction. Theoretically, the GB surface can be any ruled surface, which is mathematically defined as a surface on which every point has a straight line that lies on this surface. In reality, due to the limited array aperture and steering capability, not all ruled surfaces can be achieved by the GB scan.

FIGS. 7 and 8 are schematic illustrations of all-optical fiber scanning imaging probes 702 and 802 which can be used for MRI-compatible ultrasound probe 602 according to embodiments of the current disclosure. This is an embodiment based on a photoacoustic transmitter and a fiber-optical ultrasound receiver. Optical ultrasound transmission and receiving methods described in U.S. patent application Ser. No. 13/943,649 (incorporated herein by reference) can be used according to some embodiments of the current disclosure. As shown in FIG. 8, a single all-optical ultrasound element is in the 2D probe enclosure. The element is mechanically driven by motors with two degree of freedom, moving on the inner side of the probe coupling surface. The routine along which the ultrasound element scans can be pre-programmed based on the target structure. Furthermore, MRI compatible motors are used in the MRI-compatible ultrasound probes 702 and 802. For example, the pneumatic stepper motor described in U.S. Pub. No. 2012/0076681 (U.S. application Ser. No. 13/270,692), which is assigned to the same assignee as the current application, can be used for the above-noted mechanically driven motors to provide a fully MRI compatible ultrasound probe. The entire content of this reference is incorporated herein by reference.

Figure 9:
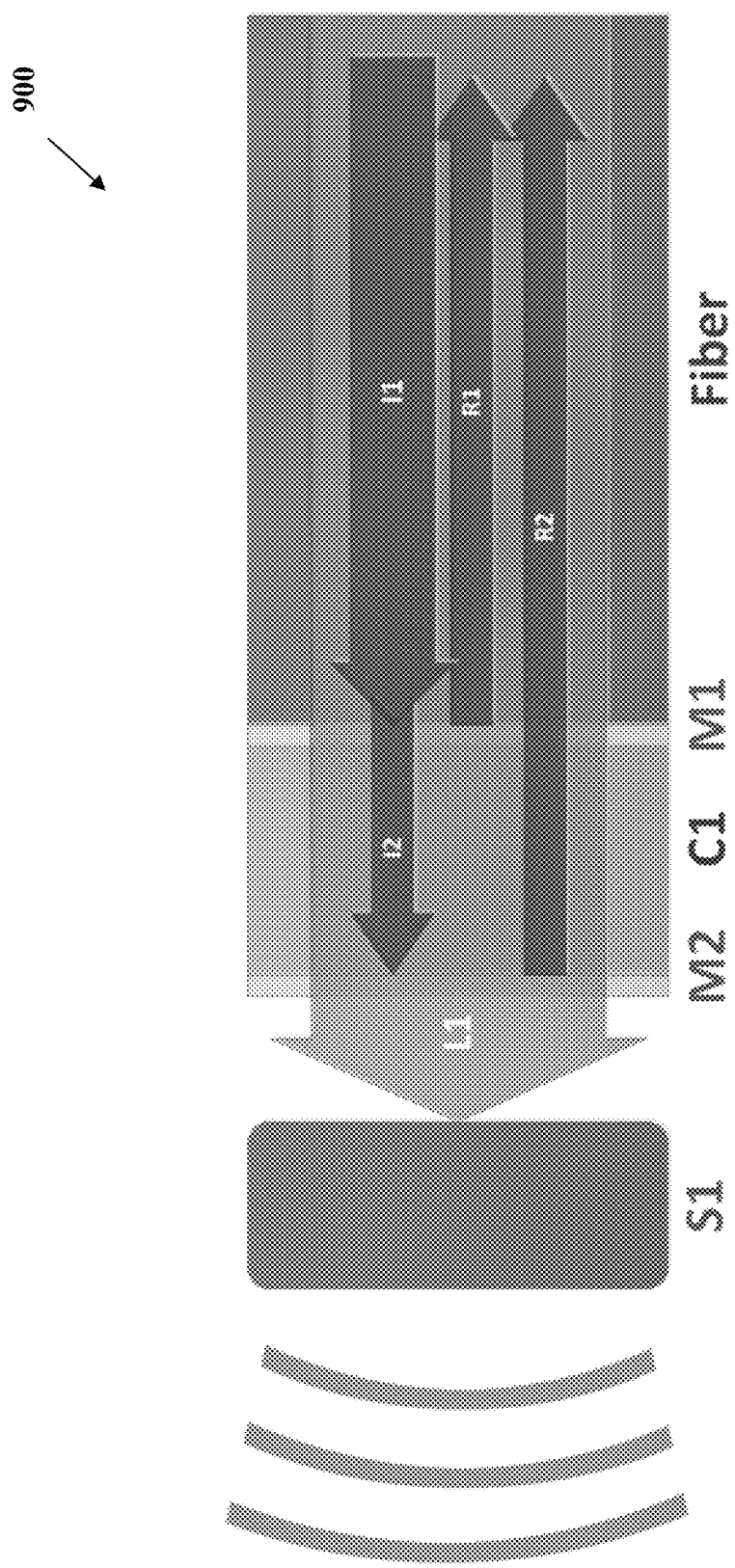
FIG. 9 is a schematic illustration of a transmit-receive end of an all-optical ultrasound transducer, according to an embodiment of the current disclosure.

FIG. 9 is a schematic illustration of an embodiment of an optical fiber for use with both transmission and detection in the MRI-compatible ultrasound probe 602. The optical fiber sensor 900 is an optical fiber based Fabry-Perot interferometer. As shown in the figure, the laser beam I1 is sent through an optical fiber. At the fiber tip the reflective layer M1, M2 and the transparent layer C1 forms a Fabry-Perot interferometer. M1 is a partially reflective layer, at which the part of the laser beam R1 is reflected and the remaining beam I2 is transmitted. At the layer M2, I2 is reflected back as R2. Both the beams R1 and R2 are reflected back, with a phase difference related to the thickness of C1. The overall backward reflection directly depends on the interference, in other words the phase delay between the beams, on the layer M1. When an ultrasound wave is incident on M2, the thickness of C1 changes with the sound wave, thus the phase delay between the two reflected beams changes as well. As a result, the ultrasound waveform can be detected by measuring the reflected laser beam amplitude.

The mirrors M1 and M2 are transparent to excitation light L1. The ultrasound transmission uses the photoacoustic (PA) effect, while reception uses a fiber-based interferometer. Therefore, in this embodiment, the transmitter and receiver can share the same optical fiber to further reduce the device footprint and complexity and provide all-optical transmission and detection. As is shown in the FIG. 9, the fiber is used to guide both the detection laser beams (l1, l2, R1, R2) and the PA excitation beam (L1). The PA beam has a wavelength of $\lambda_1$ and the detection beam has a wavelength of $\lambda_2$. The mirror M1 is transparent for $\lambda_1$ and partially reflecting for $\lambda_2$, while M2 is reflective for $\lambda_2$. (The term "transparent" is intended to mean that a sufficient amount of light L1 passes through to provide an adequate photoacoustic signal for the particular application.) As a result, the PA beam will be output from the fiber tip and absorbed by the PA element S1. S1 absorbs the laser energy and generates a photoacoustic pulse.

Figure 10:
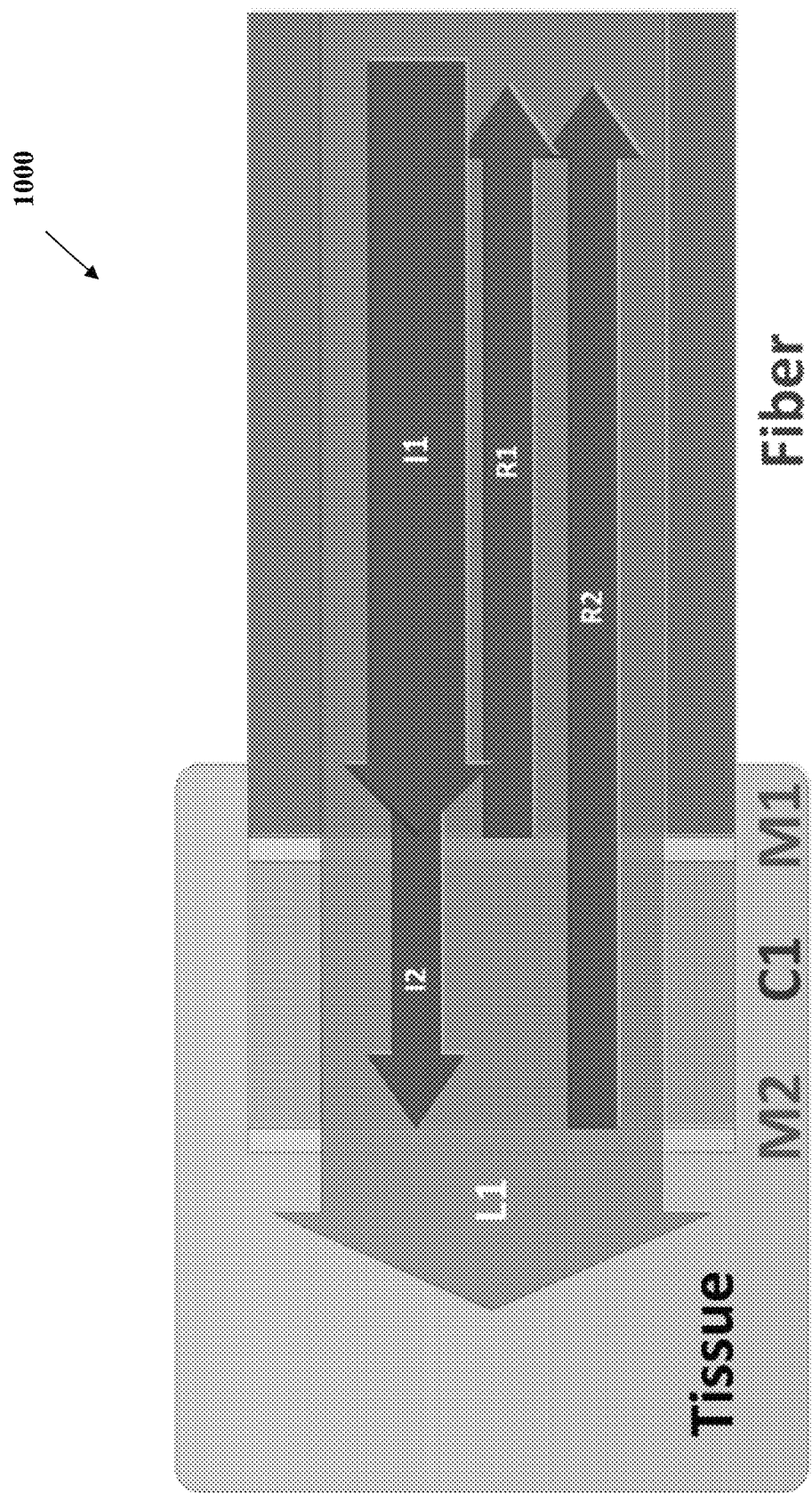
FIG. 10 is a schematic illustration of a transmit-receive end of an all-optical ultrasound transducer, according to another embodiment of the current disclosure.

FIG. 10 is a schematic illustration of another embodiment that has an optical fiber for use with both transmission and detection. In this case the optical fiber sensor 1000 is similar, or the same as, the optical fiber sensor 900. This can be similar or the same as the embodiment of FIG. 9, but without photoacoustic element S1. Depending on the applications, the PA beam can be directly delivered to the body, such as, but not limited to, tissue. The laser energy is absorbed by the tissue and generates photoacoustic signals. Consequently, in this case, the PA element S1 is not needed.

In some embodiments, the all-optical ultrasound transducer of the MRI-compatible ultrasound probe 602 has an array of a plurality of optical fibers, each of which carries optical pulses that generate photoacoustic signals in the medium of interest. Each optical fiber has a Fabry-Perot interferometer at a transmission-reception end. In this embodiment, the ultrasound controller 104 controls selection and timing of optical pulses in optical fibers of the array of the plurality of optical fibers such that a plurality of phase-controlled photoacoustic signals are generated for beam steering in a phased array of photoacoustic signals.

The embodiments illustrated and discussed in this specification are intended only to teach those skilled in the art how to make and use the invention. In describing embodiments of the disclosure, specific terminology is employed for the sake of clarity. However, the disclosure is not intended to be limited to the specific terminology so selected. The above-described embodiments of the disclosure may be modified or varied, without departing from the invention, as appreciated by those skilled in the art in light of the above teachings. It is therefore to be understood that, within the scope of the claims and their equivalents, the invention may be practiced otherwise than as specifically described. For example, it is to be understood that the present disclosure contemplates that, to the extent possible, one or more features of any embodiment can be combined with one or more features of any other embodiment.

We claim:

1. A method of obtaining an ultrasound image of a region of interest of a body under observation, comprising:
    moving an all-optical ultrasound transducer with two degrees of freedom in a two-dimensional matrix array;
    receiving, from the all-optical ultrasound transducer, at least three non-coplanar A-line signals,
        wherein the received at least three non-coplanar A-line signals start from different positions associated with the region of interest;
    generating three-dimensional ultrasound image data based on the received at least three non-coplanar A-line signals;
    identifying a surface of the region of interest based on the generated three-dimensional ultrasound image data; and
    generating a General B-mode surface (GB surface) image based on the received at least three non-coplanar A-line signals and at least one position of the surface of the region of interest.

2. The method of claim 1, wherein receiving the at least three non-coplanar A-line signals comprises electronically scanning the all-optical ultrasound transducer to each of the at least three non-coplanar A-line signals.

3. The method of claim 1, wherein the GB surface image approximates an image along a non-flat two-dimensional surface.

4. The method of claim 1, further comprising:
    transmitting at least three other non-coplanar A-line signals that correspond to the received at least three non-coplanar A-line signals.

5. The method of claim 1, wherein the received at least three non-coplanar A-line signals are oriented in different directions.

6. An ultrasound probe, comprising:
    an optical fiber configured to carry optical pulses to generate photoacoustic signals in a body of interest;
    a phased array configured to move on a bottom surface of the ultrasound probe with two degrees of freedom,
        wherein the phased array includes an all-optical ultrasound transducer configured to receive at least three non-coplanar A-line signals,
            wherein the received at least three non-coplanar A-line signals start from different positions associated with the body of interest; and
    a processor configured to:
    generate three-dimensional ultrasound image data based on the received at least three non-coplanar A-line signals, identify a surface of the body of interest based on the generated three-dimensional ultrasound image data, and generate a General B-mode surface (GB surface) image based on the received at least three non-coplanar A-line signals and at least one position of the surface of the body of interest.

7. The ultrasound probe according to claim 6, wherein the all-optical ultrasound transducer is at least one of attached to or integral with the optical fiber.

8. The ultrasound probe according to claim 6, wherein the all-optical ultrasound transducer is arranged to be separate from the optical fiber.

9. The ultrasound probe of claim 6, wherein the all-optical ultrasound transducer is pre-programmed with a routine to receive the at least three non-coplanar A-line signals.

10. The ultrasound probe of claim 6, wherein the GB surface image approximates an image along a non-flat two-dimensional surface.

11. The ultrasound probe of claim 6, wherein the all-optical ultrasound transducer comprises a set of photo-acoustic ultrasound transducer elements configured to transmit and receive ultrasound pulses optically.

12. The ultrasound probe of claim 6, wherein the all-optical ultrasound transducer is configured to transmit at least three other non-coplanar A-line signals that correspond to the received at least three non-coplanar A-line signals.

13. The ultrasound probe of claim 12, wherein the at least three other non-coplanar A-line signals are oriented in different directions.

14. An ultrasound probe, comprising:
an optical fiber configured to carry optical pulses to generate photoacoustic signals in a body of interest;
an all-optical ultrasound transducer configured to:
move with two degrees of freedom in a two-dimensional matrix array, and
receive at least three non-coplanar A-line signals,
wherein the at least three non-coplanar A-line signals start from different positions; and
a processor configured to:
generate three-dimensional ultrasound image data based on the received at least three non-coplanar A-line signals,
identify a surface of the body of interest based on the generated three-dimensional ultrasound image data, and
generate a General B-mode surface (GB surface) image based on the received at least three non-coplanar A-line signals and at least one position of the surface of the body of interest.

15. The ultrasound probe according to claim 14, wherein the all-optical ultrasound transducer is arranged to be separate from the optical fiber.

16. The ultrasound probe of claim 14, wherein the GB surface image approximates an image along a non-flat two-dimensional surface.

17. The ultrasound probe according to claim 14, wherein the all-optical ultrasound transducer is configured to transmit at least three other non-coplanar A-line signals that correspond to the received at least three non-coplanar A-line signals.

18. The ultrasound probe according to claim 17, wherein the at least three other non-coplanar A-line signals are oriented in different directions.

19. An ultrasound system, comprising:
a phased array configured to move on a bottom surface of an ultrasound probe with two degrees of freedom,
wherein the phased array includes an all-optical ultrasound transducer configured to receive at least three first non-coplanar A-line signals;
an ultrasound controller configured to:
provide control signals to the all-optical ultrasound transducer to transmit at least three second non-coplanar A-line signals and to receive the at least three first non-coplanar A-line signals,
wherein the at least three first non-coplanar A-line signals start from different positions; and
a processor configured to:
generate three-dimensional ultrasound image data based on the at least three first corresponding non-coplanar A-line signals, identify a surface of interest based on the generated three-dimensional ultrasound image data, and
generate a General B-mode surface (GB surface) image based on the at least three first non-coplanar A-line signals and at least one position of the surface of interest.

20. The ultrasound system according to claim 19, wherein the all-optical ultrasound transducer comprises a set of photo-acoustic ultrasound transducer elements configured to transmit and receive ultrasound pulses optically.

21. The ultrasound system according to claim 19, wherein the all-optical ultrasound transducer is pre-programmed with a routine to receive the at least three first non-coplanar A-line signals.

22. The ultrasound system according to claim 19, wherein the at least three first non-coplanar A-line signals are oriented in different directions.

23. The ultrasound system according to claim 19, wherein the phased array is an array of transducer elements.

24. The ultrasound system according to claim 23, wherein the array of transducer elements comprises at least one of a piezo-electric transducer, a capacitive micro-machined ultrasonic transducer (CMUT), or a photo-acoustic transducer.

25. The ultrasound system according to claim 23, wherein the ultrasound controller is further configured to:
provide the control signals to selected elements of the array of transducer elements to transmit the at least three second non-coplanar A-line signals.

26. The ultrasound system according to claim 25, wherein the ultrasound controller, to provide the control signals to the selected elements of the array of transducer elements, is configured to:
provide the control signals to the selected elements of the array of transducer elements in a selected phase relationship to provide electronic steering of the at least three first non-coplanar A-line signals.

27. An ultrasound system, comprising:
one or more memories; and
one or more processors, communicatively coupled to the one or more memories, to:
move an all-optical ultrasound transducer with two degrees of freedom in a two-dimensional matrix array;
receive, from the all-optical ultrasound transducer, at least three non-coplanar A-line signals,
wherein the at least three non-coplanar A-line signals start from different positions associated with a region of interest;
generate three-dimensional ultrasound image data based on the received at least three non-coplanar A-line signals;
identify a surface of the region of interest based on the generated three- dimensional ultrasound image data; and
generate a General B-mode surface (GB surface) image based on the received at least three non-coplanar A-line signals and at least one position of the surface of the region of interest.

28. The ultrasound system according to claim 27, wherein the one or more processors are configured to:
transmit at least three other non-coplanar A-line signals that correspond to the received at least three non-coplanar A-line signals.

29. The ultrasound system according to claim 27, wherein the one or more processors are pre-programmed with a routine to receive the at least three non-coplanar A-line signals.

30. The ultrasound system according to claim 27, wherein the received at least three non-coplanar A-line signals are oriented in different directions.

31. The ultrasound system according to claim 27, wherein the one or more processors, to receive the at least three non-coplanar A-line signals, are configured to:
  electronically scan the all-optical ultrasound transducer to each of the at least three non-coplanar A-line signals.

32. The ultrasound system according to claim 27, wherein the GB surface image approximates an image along a non-flat two-dimensional surface.

33. The ultrasound system according to claim 27,
  wherein the all-optical ultrasound transducer is an array of transducer elements.

34. The ultrasound system according to claim 33, wherein the one or more processors are further configured to:
  provide control signals to selected elements of the array of transducer elements in a selected phase relationship to provide electronic steering of the received at least three non-coplanar A-line signals.

35. The ultrasound system according to claim 33, wherein the array of transducer elements comprises at least one of a capacitive micro-machined ultrasonic transducer (CMUT), or a photo-acoustic transducer.

* * * * *